United States Patent [19]

Kawauchi et al.

[11] Patent Number: 5,652,321

[45] Date of Patent: Jul. 29, 1997

[54] COMPOSITION FOR OPTICAL MATERIALS AND USE THEREOF

[75] Inventors: Nobuya Kawauchi; Katsuyoshi Sasagawa; Seiichi Kobayashi, all of Yokohama, Japan

[73] Assignee: Mitsui Toatsu Chemicals, Inc., Tokyo, Japan

[21] Appl. No.: 550,352

[22] Filed: Oct. 30, 1995

[30] Foreign Application Priority Data

Nov. 17, 1994 [JP] Japan .................................. 6-283613
Nov. 24, 1994 [JP] Japan .................................. 6-289710

[51] Int. Cl.$^6$ .................................................. C08G 18/48
[52] U.S. Cl. ............................ 528/76; 528/85; 351/159
[58] Field of Search ........................ 528/76, 85; 351/159

[56] References Cited

U.S. PATENT DOCUMENTS 4,689,387 8/1987 Kajinoto et al. ........................ 528/76
5,475,074 12/1995 Matsuoka et al. ....................... 526/336

OTHER PUBLICATIONS

Lesiak & Maciejewski; Chem. & Applications Aliphatic Isocyanatos; J. Prakt, Chem. (1993) [abstract] 335(3), 294–6.
Kogyo Kagaky Zasshi 68(9), 1752–6(1965), "Synthesis of Polyamides Containing Disulfide Bonds".
Journal fur praktische Chemie Chemiker-Zeitung (1993), "Synthesis of Aliphatic Diisocyanates Containing Oxygen or Sulphur Bridge in Polymethylene Chain", Lesiak et al.
Chemical Abstract vol. 114: 237395t (1991), "High-reference-index plastic lens".
Chemical Abstract vol. 121:108012m (1994), "Preparation of polyisocyanates of hydrocarbons as optical materials".
Chemical Abstract vol. 112: 159987e, "Resin for plastic lenas and its preparation". (1988).
Chemical Abstract vol. 118: 14474z (1993), "Preparation of polyisocyanates as optical materials and products".
Chemical Abstract vol. 119: 140072a, "Heat–resistant polyisocyanates and optical materials and products using the same". (1993).

*Primary Examiner*—Rachel Gorr
*Attorney, Agent, or Firm*—Burns, Doane, Swecker & Mathis

[57] ABSTRACT

A composition for optical materials is herein disclosed which comprises the following two components (a) and (b):

(a) a component containing at least one of poly isocyanates represented by the formula (1)

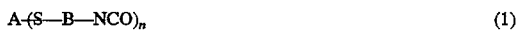

$$A\text{-(S—B—NCO)}_n \qquad (1)$$

wherein A is an alkanediyl group or an alkanetetrayl group which may contain a sulfur atom, or a dithianetetrayl group, and the alkanediyl group or the alkanetetrayl group may be substituted by a phenyl group; B is a methylene chain represented by $-\text{(CH}_2\text{)}_m-$ (m is an integer of 1 to 4) which may contain a sulfur atom, and B's may be the same or different; and n is an integer of 2 or 4, and (b) a component containing at least one of polythiols having two or more mercapto groups. The composition is useful to provide optical products such as plastic lenses, filters, substrates for recording media and optical fibers which have a very high refractive index and which are excellent in heat resistance.

6 Claims, No Drawings

COMPOSITION FOR OPTICAL MATERIALS AND USE THEREOF

BACKGROUND OF THE INVENTION

1. Field of the Invention

The present invention relates to a composition for optical materials and a use thereof. The composition for the optical materials of the present invention is a composition useful to provide optical products such as plastic lenses, filters, substrates for recording media and optical fibers which have a very high refractive index and which are excellent in heat resistance.

2. Prior Art

Plastic lenses are lightweight, less breakable, dyeable and excellent in workability of cutting, polishing and the like as compared with inorganic lenses. For these reasons, in recent years, they have been rapidly spread in the field of optical elements such as eyeglass lenses and camera lenses. However, in order to meet the needs of high fashion, the lenses are required to have decreased center thickness, edge thickness and curvature of the lenses, and in other words, it is necessary that the lenses are thin on the whole. In view of this point, for resin materials which can be used as the optical materials, a higher refractive index is demanded.

As the lenses having a high refractive index, there are already known sulfur-containing polyurethane lenses. For example, the specification of U.S. Pat. No. 4,775,733 (the publication of Japanese Patent Laid-open No. 46213/1988) has suggested polyurethane lenses comprising a polymer of a xylylene diisocyanate compound and a polythiol compound, and these lenses have been widely spread as optical lenses such as eyeglass lenses. Furthermore, as other lenses having a high refractive index, for example, the specification of U.S. Pat. No. 5,191,055 (the publication of Japanese Patent Application Laid-open No. 270859/1990) has suggested polyurethane lenses comprising a polymer of 1,2-bis[(2-mercaptoethyl)thio]-3-mercaptopropane and a polyisocyanate compound. This resin composition has been recognized to possess a high practicality, particularly a high refractive index, and therefore, it has been commercialized by many lens makers.

These polyurethane resins have a high refractive index, but they are poor in heat resistance as compared with olefin group radical polymerization type resins, e.g., DAC (diethylene glycol bisaryl carbonate) resins. Therefore, usually during post-processing such as the dyeing or surface coating of the lenses which require thermal processing at about 60° to 90° C., the lenses of the polyurethane resins are easily deformed, and hence much attention should be paid to a thermal processing temperature.

As techniques for improving the heat resistance of these polyurethane resins, there are known methods described in the publications of Japanese Patent Application Laid-open Nos. 275901/1990, U.S. Pat. No. 5,310,847 (a publication of Japanese Patent Application Laid-open No. 56525/1991) and the like. However, the polyurethane resin comprising a polymer of two kinds of aliphatic polythiol compounds and an aromatic polyisocyanate compound in Japanese Patent Application Laid-open Nos. 275901/1990 is improved in heat resistance, but the refractive index of this polyurethane resin is as low as about 1.57 to 1.61. Accordingly, it is unavoidably recognized that such the resin loses the advantage of the polyurethane lenses. Furthermore, also in a specification of U.S. Pat. No. 5,310,847 (a publication of Japanese Patent Application Laid-open No. 56525/1991), there has been disclosed a method which comprises combining a specific polythiol having a high sulfur content with a polyisocyanate to improve the heat resistance of the polyurethane resin. In this method, however, the kinds of usable polythiols are limited to compounds having a low molecular weight and a high sulfur content, and what is worse, these low-molecular weight polythiols have a strong foul odor, which makes it difficult to industrially use them.

With regard to eyeglass lens resins, the acquirement of dyeable properties thereof has heretofore been extremely important to meet the needs of high fashion. In the polyurethane resin having a high refractive index, the dyeable properties are incompatible with the heat resistance, and therefore, particularly in the case that the polyurethane resin is used as the eyeglass lenses, it has been necessary to regulate the heat resistance of the resin to be used into a suitable range.

However, the recent development of resin dyeing techniques utilizing various carriers has permitted, like the resin having a low heat resistance, the dyeing of the resin having an extremely high heat resistance which has not been dyed by a conventional dyeing method using a dye singly. Nowadays, there is a tendency that not only the high refractive index but also a high heat resistance is required for the resin as the optical material.

For the plastic lenses for use in various optical lenses such as eyeglass lenses and for compositions which can be used to manufacture these lenses, the demand of simultaneously satisfying the high heat resistance and the high refractive index is more and more strong. The improvement of the polythiol compound is not enough to achieve this object, and a polyisocyanate compound which can realize the high heat resistance and the high refractive index is necessary.

As the polyisocyanate compound and its composition which mainly intend to realize the high refractive index, for example, Japanese Patent Application Laid-open No. 153302/1990 has disclosed thiocarbamic acid S-alkyl ester lenses obtained by reacting a sulfur-containing polyisocyanate derivative having a sulfide structure or a disulfide structure with a polythiol derivative. However, in the case that the polyurethane lenses are manufactured by the use of this polyisocyanate derivative, the high refractive index can be attained by suitably selecting a combination of the polyisocyanate derivative with the polythiol derivative which is a polymerization partner, but the extremely high heat resistance which has recently been required is not so considered.

Moreover, Japanese Patent Application Laid-open No. 65193/1994 has disclosed an optical material obtained by polymerizing a mixture of a triisocyanate derivative having a sulfur atom and a polythiol derivative. However, three polymerizable functional groups of this sulfur-containing triisocyanate derivative contribute to the improvement of the heat resistance to some extent, but the content of the sulfur atom which has a high atomic refraction decreases, so that the disclosed optical material cannot always provide the satisfactory resin composition from the viewpoint of the refractive index. In particular, the polyisocyanate compound disclosed herein has a long methylene chain, and this chain is a molecular structure which disadvantageously functions in the points of the heat resistance and the refractive index. Consequently, the disclosed optical material is not sufficient to realize a resin composition having a high refractive index.

As a resin having a high heat resistance and a high refractive index, the publication of Japanese Patent Application Laid-open No. 105677/1993 has disclosed an optical material obtained by polymerizing a mixture comprising a triisocyanate derivative having a dithiolan ring in its molecule and a polythiol derivative. Additionally, in Japanese Patent Application Laid-open No. 159275/1992, there has been disclosed a 1,4-dithiane derivative substituted by two isocyanatoalkyl groups.

To obtain a polymer simultaneously satisfying the extremely high heat resistance and refractive index, however, even if either isocyanate derivative of a triisocyanate derivative and a diisocyanate derivative disclosed herein is used, the kinds of polythiol derivatives which can be used in combination are inconveniently limited.

SUMMARY OF THE INVENTION

An object of the present invention is to provide a composition for optical materials comprising a polyisocyanate compound and a polythiol compound which can provide an optical material having an extremely high refractive index and an excellent heat resistance.

Another object of the present invention is to provide plastic lenses having a high refractive index which can be obtained by polymerizing the composition.

A further object of the present invention is to provide a novel sulfur-containing isocyanate for use in the preparation of plastic lenses.

The present inventors have conducted an intense investigation on the basis of a conception that, in order to solve the above-mentioned problems, a polyisocyanate having a structure which can simultaneously satisfy a structurally high refractive index and heat resistance is necessary, and the polyisocyanate compound having such physical properties is (1) a polyisocyanate compound capable of minimizing the number of isocyanate groups which are disadvantageous for the refractive index to realize the high refractive index, and capable of realizing the heat resistance by virtue of a central molecular skeleton or a polythiol derivative which is a polymerization partner, or (2) a compound obtained by introducing sulfur atoms, for realizing the high refractive index, corresponding to the number of isocyanate groups into a polyisocyanate derivative having many isocyanate groups and capable of heightening a crosslink density of a polymer to improve the heat resistance.

As a result, it has been found that as the polyisocyanate compound, by the use of a polyisocyanate compound obtained by introducing a structure containing a large number of chemically stable sulfur atoms into a polyisocyanate compound having minimum isocyanate groups sufficient to form a resin, i.e., two functional groups and/or a polyisocyanate compound having thioalkyl isocyanate groups sufficient to realize the high heat resistance as polymerizable functional group units, lenses having an extremely high refractive index and an excellent heat resistance can be obtained. In consequence, the present invention has been completed. That is to say, the present invention is directed to a composition for optical materials which comprises the following two components (a) and (b):

(a) a component containing at least one polyisocyanate represented by the following formula (1):

wherein A is an alkanediyl group or an alkanetetrayl group which may contain a sulfur atom, or a dithianetetrayl group, and the alkanediyl group or the alkanetetrayl group may be substituted by a phenyl group; B is a methylene chain represented by $-(CH_2)_m-$ (m is an integer of 1 to 4) which may contain a sulfur atom, and Bs may be the same or different; and n is an integer of 2 or 4, and (b) a component containing at least one of polythiols having two or more mercapto groups.

Furthermore, the present invention is also concerned with plastic lenses having a high refractive index obtained by polymerizing this composition for optical materials.

The composition for the optical materials which comprises a diisocyanate or a tetraisocyanate containing a sulfur atom according to the present invention is a composition useful to provide optical products such as plastic lenses, filters, substrates for recording media and optical fibers having a very high refractive index and an excellent heat resistance.

DETAILED DESCRIPTION OF THE PREFERRED EMBODIMENTS

Next, the present invention will be described in detail.

A diisocyanate compound of n=2 in formula (1) which can be used in the present invention has a higher sulfur content as compared with the triisocyanate derivative having a sulfur atom disclosed in Japanese Patent Application Laid-open No. 65193/1994, and such a diisocyanate compound is extremely advantageous in point of a refractive index. Furthermore, the heat resistance of a resin composition prepared from this diisocyanate compound can be obtained by suitably modifying the molecular structure of the isocyanate, or suitably selecting a polythiol compound which is a polymerization partner.

The preferable diisocyanate compound is a polyisocyanate represented by the following formula (2):

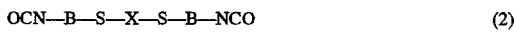

wherein X is a lower alkanediyl group having 1 to 4 carbon atoms which may contain a sulfur atom, and this alkanediyl group may be substituted by a phenyl group; and B is a methylene chain represented by $-(CH_2)_m-$ (m is an integer of 1 to 4) which may contain a sulfur atom, and Bs may be the same or different.

Of the compounds represented by the formula (1) which can be used in the present invention, a tetraisocyanate compound of n=4 is much more excellent in heat resistance as compared with the triisocyanate derivative having a sulfur atom disclosed in Japanese Patent Application Laid-open No. 65193/1994 and the 1,4-dithiane derivative substituted by two isocyanate alkyl groups described in Japanese Patent Application Laid-open No. 159275/1992. The preferred tetraisocyanate compound is a polyisocyanate represented by the following formula (3):

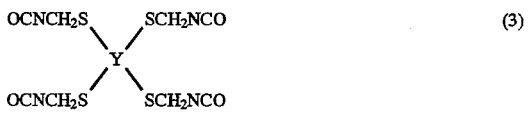

wherein Y is a lower alkanetetrayl group having 1 to 4 carbon atoms which may contain a sulfur atom or a dithianetetrayl group.

As the isocyanate compound which can be used in the present invention, a tetraisocyanate derivative is more preferable in view of the heat resistance and ease of manufacturing.

Typical examples of the polyisocyanate represented by formula (1) which can be used in the present invention include bis(isocyanatomethylthio)methane, bis (isocyanatomethylthio)methylthiomethane, bis(2-isocyanatoethylthio)methane, bis(3-isocyanatopropylthio) methane, isocyanatomethylthio(2-isocyanatoethylthio) methane, 2-isocyanatoethylthio(3-isocyanatopropylthio) methane, bis(isocyanatomethylthio)phenylmethane, bis(2-isocyanatoethylthio)phenylmethane, bis(3-isocyanatopropylthio)phenylmethane, 1,2-bis (isocyanatomethylthio)ethane, 1,2-bis(2-isocyanatoethylthio)ethane, 1-isocyanatomethylthio-2-(2-isocyanatoethylthio)ethane, 1-isocyanatoethylthio-2-(3-isocyanatopropylthio)ethane, bis (isocyanatomethylthioethyl) sulfide, tetrakis (isocyanatomethylthio)methane, 1,1,2,2-tetrakis (isocyanatomethylthio)ethane, 2,2,5,5-tetrakis (isocyanatomethylthio)-1,4-dithiane and 2,2,5,5-tetrakis (isocyanatomethylthio)-1,3-dithiane.

Above all, preferable examples include bis (isocyanatomethylthio)methane, bis(isocyanatomethylthio) phenylmethane, 1,2-bis(isocyanatomethylthio)ethane, 1,2-bis(2-isocyanatoethylthio)ethane, bis (isocyanatomethylthioethyl) sulfide, 1,1,2,2-tetrakis (isocyanatomethylthio)ethane and 2,2,5,5-tetrakis (isocyanatomethylthio)-1,4-dithiane, and more preferable examples include bis(isocyanatomethylthio)methane, 1,2-bis(isocyanatomethylthio)ethane, and the most preferable example is bis(isocyanatomethylthio)methane.

The above-mentioned component (a) may contain polyisocyanate compounds other than the polyisocyanates represented by formula (1) for the purpose of suitably improving the physical properties of the optical materials. In this case, the amount of the polyisocyanate compound to be used represented by formula (1) is 60 mol % or more, preferably 70 mol % or more, more preferably 80 mol % or more of the total polyisocyanates.

Typical examples of the polyisocyanate compound other than the polyisocyanates represented by formula (1) include o-xylylene diisocyanate, m-xylylene diisocyanate, p-xylylene diisocyanate, α, α,α',α'-tetramethyl-p-xylylene diisocyanate, α,α,α',α'-tetramethyl-m-xylylene diisocyanate, 1,3,5-tris(isocyanatomethyl)benzene, and nuclear chlorides, bromides, methylated compounds and ethylated compounds thereof such as 4-chloro-m-xylylene diisocyanate, 4,5-dichloro-m-xylylene diisocyanate, 2,3,5,6-tetrabromo-p-xylylene diisocyanate, 4-methyl-m-xylylene diisocyanate, 4-ethyl-m-xylylene diisocyanate, hexamethylene diisocyanate, isophorone diisocyanate, norbornene diisocyanate, methylenebis(cyclohexylisocyanate), bis (isocyanatomethyl)cyclohexane, 1,3-dithiolane-4,5-diisocyanate, 4,5-bis(isocyanatomethyl)-1,3-dithiolane and tris(isocyanatomethylthio)methane. Some of these polyisocyanate compounds are now on the market.

The above-mentioned component (b) comprises at least one polythiol having two or more mercapto groups. Examples of these polythiols include aliphatic polythiols such as methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, bicyclo[2.2.1] hepta-exo-cis-2,3-dithiol, 1,1-bis(mercaptomethyl) cyclohexane, bis(2-mercaptoethyl) thiomalate, (2-mercaptoethyl)-2,3-dimercaptosuccinate, 2,3-dimercapto-1-propanol-(2-mercaptoacetate), 2,3-dimercapto-1-propanol-(3-mercaptopropionate), diethylene glycol bis(2-mercaptoacetate), diethylene glycol bis(3-mercaptopropionate), 1,2-dimercaptopropyl methyl ether, 2,3-dimercaptopropyl methyl ether, 2,2-bis (mercaptomethyl)-1,3-propanedithiol, bis(2-mercaptoethyl) ether, ethylene glycol bis(2-mercaptoacetate), ethylene glycol bis(3-mercaptopropionate), trimethylolpropane bis(2-mercaptoacetate), trimethylolpropane bis(3-mercaptopropionate), pentaerythritol tetrakis(2-mercaptoacetate), pentaerythritol tetrakis(3-mercaptopropionate), 1,2-bis(2-mercaptoethylthio)-3-mercaptopropane and 4,8-bis(mercaptomethyl)-3,6,9-trithia-1,11-undecanedithiol; aromatic polythiols such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl) benzene, 1,2-bis(mercaptoethyl)benzene, 1,3-bis (mercaptoethyl)benzene, 1,4-bis(mercaptoethyl)benzene, 1,2-bis(mercaptomethyleneoxy)benzene, 1,3-bis (mercaptomethyleneoxy)benzene, 1,4-bis (mercaptomethyleneoxy)benzene, 1,2-bis (mercaptoethyleneoxy)benzene, 1,3-bis (mercaptoethyleneoxy)benzene, 1,4-bis (mercaptoethyleneoxy)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl) benzene, 1,3,5-tris(mercaptomethyl)benzene, 1,2,3-tris (mercaptoethyl)benzene, 1,2,4-tris(mercaptoethyl)benzene, 1,3,5-tris(mercaptoethyl)benzene, 1,2,3-tris (mercaptomethyleneoxy)benzene, 1,2,4-tris (mercaptomethyleneoxy)benzene, 1,3,5-tris (mercaptomethyleneoxy)benzene, 1,2,3-tris (mercaptoethyleneoxy)benzene, 1,2,4-tris (mercaptoethyleneoxy)benzene, 1,3,5-tris (mercaptoethyleneoxy)benzene, 1,2,3,4-tetramercaptobenzene, 1,2,3,5-tetramercaptobenzene, 1,2,4, 5-tetramercaptobenzene, 1,2,3,4-tetrakis(mercaptomethyl) benzene, 1,2,3,5-tetrakis(mercaptomethyl)benzene, 1,2,4,5-tetrakis(mercaptomethyl)benzene, 1,2,3,4-tetrakis (mercaptoethyl)benzene, 1,2,3,5-tetrakis(mercaptoethyl) benzene, 1,2,4,5-tetrakis(mercaptoethyl)benzene, 1,2,3,4-tetrakis(mercaptomethyleneoxy)benzene, 1,2,3,5-tetrakis (mercaptomethyleneoxy)benzene, 1,2,4,5-tetrakis (mercaptomethyleneoxy)benzene, 1,2,3,4-tetrakis (mercaptoethyleneoxy)benzene, 1,2,3,5-tetrakis (mercaptoethyleneoxy)benzene, 1,2,4,5-tetrakis (mercaptoethyleneoxy)benzene, 2,2'-dimercaptobiphenyl, 4,4'-dimercaptobiphenyl, 4,4'-dimercaptobibenzyl, 2,5-toluenedithiol, 3,4-toluenedithiol, 1,4-naphthalenedithiol, 1,5-naphthalenedithiol, 2,6-naphthalenedithiol, 2,7-naphthalenedithiol, 2,4-dimethylbenzene-1,3-dithiol, 4,5-dimethylbenzene-1,3-dithiol, 9,10-anthracenedimethanethiol, 1,3-di(p-methoxyphenyl) propane-2,2-dithiol, 1,3-diphenylpropane-2,2-dithiol, phenylmethane-1,1-dithiol and 2,4-di(p-mercaptophenyl) pentane; polythiols containing heterocyclic ring such as 2-methylamino-4,6-dithiol-sym-triazine, 2-ethylamino-4,6-dithiol-symtriazine, 2-amino-4,6-dithiol-sym-triazine, 2-morpholino-4,6-dithiol-sym-triazine, 2-cyclohexylamino-4,6-dithiol-sym-triazine, 2-methoxy-4,6-dithiol-sym-triazine, 2-phenoxy-4,6-dithiol-sym-triazine, 2-thiobenzeneoxy-4,6-dithiol-sym-triazine, 2-thiobutyloxy-4,6-dithiol-sym-triazine and 2,5-bis(mercaptomethyl)-1,4-dithiane; aromatic polythiols containing a sulfur atom in addition to the mercapto group such as 1,2-bis (mercaptomethylthio)benzene, 1,3-bis(mercaptomethylthio) benzene, 1,4-bis(mercaptomethylthio)benzene, 1,2-bis (mercaptoethylthio)benzene, 1,3-bis(mercaptoethylthio) benzene, 1,4-bis(mercaptoethylthio)benzene, 1,2,3-tris (mercaptomethylthio)benzene, 1,2,4-tris (mercaptomethylthio)-benzene, 1,3,5-tris (mercaptomethylthio)benzene, 1,2,3-tris(mercaptoethylthio) benzene, 1,2,4-tris(mercapto-ethylthio)benzene, 1,3,5-tris (mercaptoethylthio)benzene, 1,2,3,4-tetrakis (mercaptomethylthio)benzene, 1,2,3,5-tetrakis (mercaptomethylthio)benzene, 1,2,4,5-tetrakis (mercaptomethylthio)benzene, 1,2,3,4-tetrakis (mercaptoethylthio)benzene, 1,2,3,5-tetrakis (mercaptoethylthio)benzene, 1,2,4,5-tetrakis (mercaptoethylthio)benzene and these compounds having an alkylated nucleus; aliphatic polythiols having a sulfur atom in addition to the mercapto group such as bis (mercaptomethyl) sulfide, bis(mercaptoethyl) sulfide, bis (mercaptopropyl) sulfide, bis(mercaptomethylthio)methane, bis(2-mercaptoethylthio)methane, bis(3-mercaptopropylthio)methane, 1,2-bis(mercaptomethylthio) ethane, 1,2-bis(2-mercaptoethylthio)ethane, 1,2-bis(3-mercaptopropylthio)ethane, 1,3-bis(mercaptomethylthio) propane, 1,3-bis(2-mercaptoethylthio)propane, 1,3-bis(3-mercaptopropylthio)propane, 1,2,3-tris (mercaptomethylthio)propane, 1,2,3-tris(2-mercaptoethylthio)propane, 1,2,3-tris(3-mercaptopropylthio)propane, tetrakis (mercaptomethylthiomethyl)methane, tetrakis(2-mercaptoethylthiomethyl)methane, tetrakis(3-mercaptopropylthiomethyl)methane, bis(2,3-dimercaptopropyl) sulfide, 2,5-dimercapto-1,4-dithiane, thioglycolates and mercaptopropionates thereof, hydroxymethyl sulfide bis(2-mercaptoacetate), hydroxymethyl sulfide bis(3-mercaptopropionate), hydroxyethyl sulfide (2-mercaptoacetate), hydroxyethyl sulfide bis(3-mercaptopropionate), hydroxypropyl sulfide bis(2-mercaptoacetate), hydroxypropyl sulfide bis(3-mercaptopropionate), 2-mercaptoethyl ether bis(2-mercaptoacetate), 2-mercaptoethyl ether bis(3-mercaptopropionate), 1,4-dithiane-2,5-diol bis(2-mercaptoacetate), 1,4-dithiane-2,5-diol bis(3-mercaptopropionate), bis(2-mercaptoethyl) thiodiglycolate, bis(2-mercaptoethyl) thiodipropionate, bis(2-mercaptoethyl) 4,4-thiodibutylate, bis(2-mercaptoethyl) dithiodiglcolate, bis(2-mercaptoethyl) dithiodipropionate, bis(2-mercaptoethyl) 4,4-dithiodibutylate, bis(2,3-dimercaptopropyl) thiodiglycolate, bis(2,3-dimercaptopropyl) thiodipropionate, bis(2,3-dimercaptopropyl) dithioglycolate and bis(2,3-dimercaptopropyl) dithiodipropionate; and heterocyclic compounds having a sulfur atom in addition to the mercapto group such as 3,4-thiophenedithiol and 2,5-dimercapto-1,3, 4-thiadiazole. Furthermore, these polythiols which are substituted by halogens such as chlorine and bromine may also be used.. They may be used singly or as a mixture of two or more thereof.

Of these polythiols, preferable are 2,2-bis (mercaptomethyl)-1,3-propanedithiol, 1,2-bis(2-mercaptoethylthio)-3-mercaptopropane, 4,8-bis (mercaptomethyl)-3,6,9-trithia-1,11-undecanedithiol and 1,2,4-tris(mercaptomethyl)benzene.

Some of the polyisocyanates represented by formula (1) can be prepared by known methods. For example, bis (isocyanatomethylthio)methane and 1,2-bis (isocyanatomethylthio)ethane can be prepared by a method described in J. Prakt. Chem., 335, p. 294–296 (1993). Bis(isocyanatomethylthio)methane can be obtained by reacting bis(hydrazinocarbonylmethylthio)methane with sodium nitrite in diluted hydrochloric acid, and then carrying out Curtius rearrangement in hot benzene. 1,2-Bis (isocyanatomethylthio)ethane can also be prepared in the same manner.

Furthermore, bis(hydrazinocarbonylmethylthio)methane can be obtained by treating easily commercially available methylenebisthioglycolic acid in accordance with a process described in GB 1129085, i.e., by reacting methylenebisthioglycolic acid with ethanol in the presence of an acid catalyst under heating reflux to form a bisethyl ester derivative, and further reacting this bisethyl ester derivative with hydrazine hydrate under ice cooling.

Of the isocyanate compounds suitable for component (a) in the composition for the optical materials of the present invention, the polyisocyanate compounds represented by the following formula (4) are novel compounds:

$$Z-S-B'-NCO)_n \qquad (4)$$

wherein Z is any one of the following groups;

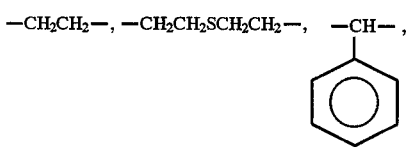

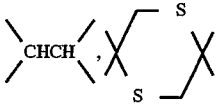

B' is —CH$_2$— or —CH$_2$CH$_2$—; and n is an integer of 2 or 4, with the proviso that when Z is —CH$_2$CH$_2$—, B' is —CH$_2$CH$_2$—.

Next, the preparation procedure of a novel isocyanate compound will be described.

1,2-Bis(2-isocyanatoethylthio)ethane represented by the following formula (5):

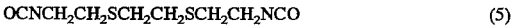

$$OCNCH_2CH_2SCH_2CH_2SCH_2CH_2NCO \qquad (5)$$

can be prepared from easily commercially available ethylenebis(thiopropionic acid) in accordance with the following procedure.

In the first place, ethylenebis(thiopropionic acid) is reacted with a lower alcohol in the presence of a suitable acid catalyst to be converted into an ester derivative. As the acid catalyst, sulfuric acid, hydrochloric acid, p-toluenesulfonic acid or the like can be used, and as the lower alcohol, methanol, ethanol, propanol or the like can be exemplified. The reaction may be carried out, utilizing the used alcohol as a solvent, or in a solvent such as toluene or benzene. Water formed during the reaction may be removed by the use of a dehydrating agent such as anhydrous sodium sulfate or molecular sieves, or may be subjected to azeotropic dehydration using a Dean Stark device in a solvent such as toluene. The reaction is practicable between room temperature and the boiling point of the solvent, but it is desirable to carry out the reaction under reflux.

The thus obtained bisester derivative is then reacted with hydrazine hydrate, thereby obtaining 1,2-bis(2-hydrazinocarbonylethylthio)ethane.

At this time, as a reaction solvent, any of methanol, ethanol, propanol, butanol, THF, dioxane and water can be used, but it is desirable to use a lower alcohol in which the bisester derivative as the raw material dissolves and the product precipitates. With regard to a reaction temperature, the reaction can be preferably accomplished between 0° C. and the boiling point of the solvent, but it is desirable to carry out the reaction at room temperature or less. Next, 1,2-bis(2-hydrazinocarbonylethylthio)ethane is reacted with a nitrite in a dilute acid, and then subjected to Curtius rearrangement under heating conditions to obtain 1,2-bis(2-isocyanatoethylthio)ethane. As the dilute acid, an aqueous dilute hydrochloric acid solution or an aqueous dilute sulfuric acid solution can be used, and this dilute acid can also be used together with a solvent which does not disturb the reaction. No particular restriction is put on a reaction temperature, so far as it does not bring about the Curtius rearrangement reaction, but it is preferably in the range of 0° to 10° C.

No particular restriction is put on the solvent for the Curtius rearrangement, so far as it does not react with the product, but preferable are benzene and toluene. The reaction is practicable at an optional temperature between room temperature and the boiling point of the solvent.

Bis[2-(isocyanatomethylthio)ethyl]sulfide represented by the following formula (6) can be prepared as follows:

OCNCH₂SCH₂CH₂SCH₂CH₂SCH₂NCO    (6)

For example, bis(2-mercaptoethyl) sulfide which is easily commercially available is reacted with a halogenated lower alkyl acetate in the presence of a base to obtain bis(2-alkyloxycarbonylmethylthioethyl) sulfide. Examples of the usable base include potassium hydroxide, sodium hydroxide, potassium carbonate and tri-ethylamine. No particular restriction is put on the solvent, so far as it does not disturb the reaction, but examples of the preferable solvent include water, ethanol, methyl ethyl ketone and methyl isobutyl ketone. The thus obtained bis(2-alkyloxycarbonylmethylthioethyl) sulfide may be purified singly or may be directly fed to a subsequent reaction.

Next, the bis(2-alkyloxycarbonylmethylthioethyl) sulfide is reacted with hydrazine hydrate to obtain bis(2-hydrazinocarbonylmethylthioethyl) sulfide. At this time, methanol, ethanol, propanol, butanol, THF, dioxane, water or the like can be used as a reaction solvent, but the employment of a lower alcohol is desirable. The reaction can be carried out between 0° C. and the boiling point of the solvent, but it is desirable to do the reaction at a temperature between 3° C. and room temperature.

Furthermore, this bis(2-hydrazinocarbonylmethylthioethyl) sulfide can be reacted with a nitrite in a dilute acid, followed by Curtius rearrangement under heating conditions, thereby obtaining bis[2-(isocyanatomethylthio)ethyl sulfide.

Here, as the dilute acid, an aqueous dilute hydrochloric acid solution or an aqueous dilute sulfuric acid solution can be used, and this dilute acid can also be used together with a solvent which does not disturb the reaction. No particular restriction is put on a reaction temperature, so far as it does not bring about the Curtius rearrangement reaction, but it is preferably in the range of 0° to 10° C. No particular restriction is put on the solvent for the Curtius rearrangement, so far as it does not react with the product, but preferable are benzene and toluene. The reaction is practicable at an optional temperature between room temperature and the boiling point of the solvent.

Bis(isocyanatomethylthio)phenylmethane represented by the following formula (7) can be prepared by the undermentioned procedure:

OCNCH₂SCHSCH₂NCO    (7)

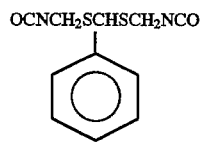

For example, a lower alkyl thioglycolate is reacted with benzaldehyde in the presence of an acid catalyst to obtain a lower alkyl (benzylidenedithio)diacetate derivative. Next, the thus obtained derivative is reacted with hydrazine hydrate to obtain (benzylidenedithio) bis (hydrazinocarbonylmethane). However, the above-mentioned lower alkyl (benzylidenedithio)diacetate derivative may be purified singly or may be directly fed to the subsequent reaction. As a reaction solvent, any of methanol, ethanol, propanol, butanol, THF, dioxane, water and the like can be used, but the employment of a lower alcohol is desirable. The reaction can be carried out between 0° C. and the boiling point of the solvent, but it is desirable to do the reaction at a temperature between 3° C. and room temperature.

Furthermore, this (benzylidenedithio) bis (hydrazinocarbonylmethane) can be reacted with a nitrite in a dilute acid, followed by Curtius rearrangement under heating conditions, thereby obtaining bis (isocyanatomethylthio)phenylmethane. As the dilute acid, an aqueous dilute hydrochloric acid solution or an aqueous dilute sulfuric acid solution can be used, and this dilute acid can also be used together with a solvent which does not disturb the reaction. No particular restriction is put on a reaction temperature, so far as it does not bring about the Curtius rearrangement reaction, but it is preferably in the range of 0° to 10° C. No particular restriction is put on the solvent for the Curtius rearrangement, so far as it does not react with the product, but preferable are benzene and toluene. The reaction is practicable at an optional temperature between room temperature and the boiling point of the solvent.

1,1,2,2-Tetrakis(isocyanatomethylthio)ethane represented by the following formula (8) can be prepared as follows:

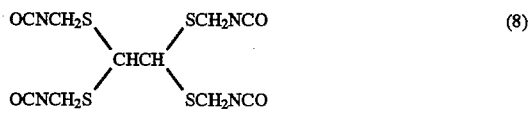

For example, easily commercially available ethanediiridenetetrakisthioacetic acid is converted into a tetrakis lower alkyl ester derivative with a suitable lower alkyl esterifying agent.

At this time, the esterification can be carried out by the use of an acid catalyst such as p-toluenesulfonic acid, sulfuric acid or hydrochloric acid and a lower alcohol, a dialkyl sulfate, diazomethane, an alkyl iodide or the like, but the employment of the acid catalyst and the lower alcohol or diazomethane is desirable. In the reaction, a solvent such as ethyl ether or a lower alcohol which does not disturb the reaction can be optionally used.

Next, this tetrakis ester derivative is reacted with hydrazine hydrate to obtain 1,1,2,2-tetrakis (hydrazinocarbonylmethylthio)ethane. At this time, as a reaction solvent, any of methanol, ethanol, propanol, butanol, THF, dioxane, water and the like can be used, but it is desirable to use a lower alcohol in which the tetrakis ester derivative as the raw material dissolves and the product precipitates. The reaction can be carried out between 0° C. and the boiling point of the solvent, but it is desirable to do the reaction at a temperature of room temperature or less.

Furthermore, this 1,1,2,2-tetrakis (hydrazinocarbonylmethylthio)ethane can be reacted with a nitrite in a dilute acid, followed by Curtius rearrangement under heating conditions, thereby obtaining 1,1,2,2-tetrakis (isocyanatomethylthio)ethane. In the reaction with the nitrite, as the dilute acid, an aqueous dilute hydrochloric acid solution or an aqueous dilute sulfuric acid solution can be used, and this dilute acid can also be used together with a solvent which does not disturb the reaction. No particular restriction is put on a reaction temperature, so far as it does not bring about the Curtius rearrangement reaction, but it is preferably in the range of 0° to 10° C.

No particular restriction is put on the solvent for the Curtius rearrangement, so far as it does not react with the product, but preferable are benzene and toluene. The reaction is practicable at an optional temperature between room temperature and the boiling point of the solvent.

2,2,5,5-Tetrakis(isocyanatomethylthio)-1,4-dithiane represented by the following formula (9) can be prepared in the same manner as above:

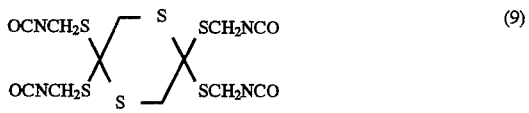

That is to say, in accordance with A. Schoberl et al., Ann. Chem., 595, p. 101 (1955), thioglycolic acid is condensed in the presence of a hydrochloric acid catalyst to form 2,2,5, 5-tetrakis(carboxymethylthio)-1,4-dithiane, and this product is then converted into a tetrakis lower alkyl ester derivative with a suitable lower alkyl esterifying agent. The esterification can be carried out by the use of a moderate acid catalyst, a lower alcohol, a dialkyl sulfate, diazomethane, an alkyl iodide or the like, but the employment of the acid catalyst and the lower alcohol or diazomethane is desirable. In the reaction, a solvent such as toluene, benzene or a lower alcohol which does not disturb the reaction can be optionally used.

Next, this tetrakis ester derivative is reacted with hydrazine hydrate to obtain 2,2,5,5-tetrakis (hydrazinocarbonylmethylthio)-1,4-dithiane. At this time, as a reaction solvent, any of methanol, ethanol, propanol, butanol, THF, dioxane, water and the like can be used, but the employment of a lower alcohol is preferable. The reaction can be carried out between 0° C. and the boiling point of the solvent, but it is desirable to do the reaction at a temperature of room temperature or less.

Furthermore, this 2,2,5,5-tetrakis (hydrazinocarbonylmethylthio)-1,4-dithiane can be reacted with a nitrite in a dilute acid, followed by Curtius rearrangement under heating conditions, thereby obtaining 2,2,5,5-tetrakis(isocyanatomethylthio)-1,4-dithiane.

In the reaction with the nitrite, as the dilute acid, an aqueous dilute hydrochloric acid solution or an aqueous dilute sulfuric acid solution can be used, and this dilute acid can also be used together with a solvent which does not disturb the reaction. No particular restriction is put on a reaction temperature, so far as it does not bring about the Curtius rearrangement reaction, but it is preferably in the range of 0° to 10° C.

No particular restriction is put on the solvent for the Curtius rearrangement, so far as it does not react with the product, but preferable are benzene and toluene. The reaction is practicable at an optional temperature between room temperature and the boiling point of the solvent.

The use ratio of the respective components in the composition of the present invention, i.e., the ratio of the component (a) to the component (b) is in the range of 0.5 to 1.5, preferably 0.6 to 1.4, more preferably 0.7 to 1.3 in terms of NCO/SH ratio.

To the composition of the present invention, some additives may be suitably added if necessary, and examples of the additives include a polymerization catalyst for accelerating a polymerization reaction, an ultraviolet light absorber, an antioxidant, a coloring inhibitor, a fluorescent dye, a light stabilizer and an oil-soluble dye for the improvement of weathering resistance. Furthermore, as needed, an internal releasing agent may also be added thereto.

The lenses of the present invention can be obtained by adding, if necessary, a polymerization catalyst and some additives to the composition containing the components (a) and (b) of the present invention, sufficiently defoaming the mixture, and then carrying out a known cast polymerization, i.e., pouring a mixed solution into a mold comprising the combination of a glass mold or a metallic mold and a resin gasket, heating and curing the same. At this time, in order to facilitate the release of a molded resin from the mold, a release treatment may be given to the mold.

The polymerization temperature and the polymerization time in the cast polymerization depend upon the composition of the monomers, the kinds and amounts of additives, but they are such that heating is begun from a temperature of 5° to 20° C. and up to a temperature of about 100° to 130° C. is reached in a period of 8 to 30 hours.

In order to accomplish the prevention of reflection, the increase of hardness, the improvement of wear resistance and chemical resistance, the impartment of fog resistance and fashion sense, and the like, the lenses obtained by the present invention, if necessary, can be subjected to a physical or a chemical treatment such as surface polishing, an antistatic treatment, a hard coating treatment, a nonreflective coating treatment, a dyeing treatment or a dimming treatment.

The lenses obtained by the present invention can be easily dyed in water or a solvent by the use of a usual disperse dye. At the time of the dyeing, a carrier which is a dyeing assistant may be added to a dye bath in order to facilitate the dyeing.

The sulfur-containing urethane resin obtained by curing the composition of the present invention has an extremely low dispersibility, a high refractive index and a low water absorption, is colorless, transparent and lightweight, and is excellent in heat resistance, weather resistance, impact resistance and surface hardness. Accordingly, the urethane resin is suitable for materials of optical elements such as eyeglass lenses and camera lenses, glazing materials, coating materials, and materials of adhesives.

Next, the present invention will be described in more detail with reference to examples, but the scope of the present invention should not be limited to these examples at all. In the examples, part and parts mean part by weight and parts by weight, respectively. The performance of obtained lenses was evaluated by the following tests.

Refractive index and Abbe's number: They were measured at 20° C. by the use of a Pulfrich refractometer.

Appearance: Coloring and transparency were observed with the naked eye.

Heat resistance: A load of 5 g was applied to each test piece by the use of a thermomechanical analyzer, TAS300 (made by Rigaku Denki Co., Ltd.), and then heated at 2.5° C./min. Afterward, a heat deformation start temperature was measured.

Dyeability: Each plate having a thickness of 9 mm was immersed and dyed at 95° C. for 5 minutes in each of 5 g/l aqueous dyeing solutions of ML-Yellow, ML-Red and ML-Blue which were disperse dyes for plastic lenses made by Mitsui Toatsu Dye Inc. After the dyeing, transmittance was then measured within 400 to 700 nm by the use of a spectrophotometer, U-2000 (Hitachi, Ltd.). As total evaluation, a sample having a good dyeability was represented by "o", and a sample having a poor dyeability or no dyeability was represented by "x".

Heat resistance of dye: Each sample lens was immersed in a dye bath at 95° C. for 5 minutes, and it was then visually observed whether or not the lens was deformed.

Water absorption: Each test piece was prepared in accordance with JIS-K-7209, and then immersed in water for 48 hours. Afterward, a weight change was calculated to determine the water absorption.

Surface hardness: A pencil hardness was measured by the use of a pencil scratching tester for coating of JIS-K-5401.

EXAMPLE 1

Preparation of 1,2-bis(isocyanatoethylthio)ethane

In a mixed solvent of 150 ml of toluene and 300 ml of ethanol was dissolved 25 g of commercially available ethylenebis(thiopropionic acid), and one drop of concentrated sulfuric acid was then added thereto. Next, reaction was carried out for 4 hours under heating reflux, while dehydration was done by molecular sieves (4A).

The reaction solution was cooled to room temperature, and most of ethanol was then distilled off by an evaporator. Next, the solution was washed with 50 ml of a saturated sodium hydrogencarbonate solution twice, and then dried over anhydrous sodium sulfate. Afterward, the solution was concentrated under reduced pressure to obtain light yellow oily crude ethylenebis(ethyl thiopropionate).

This compound was dissolved in 50 ml of ethanol, and 12.2 g of hydrazine monohydrate was added dropwise thereto, while a solution temperature of 5° C. was maintained. After 2 hours, the produced white crystalline 1,2-bis (hydrazinocarbonylethylthio)ethane was collected by filtration. Next, the collected crystals were washed with 10 ml of cold ethanol twice. After drying, the dried material was dissolved in 18 ml of water, and then cooled to 5° C. Afterward, 6.7 g of concentrated hydrochloric acid was added dropwise. Furthermore, a solution obtained by dissolving 4.2 g of sodium nitrite in 8 ml of water was added dropwise thereto. After 30 minutes, 30 ml of benzene was added thereto, and the solution was then heated up to room temperature, while vigorously stirred. Next, the resulting organic layer was separated, dried over anhydrous magnesium sulfate, and then added dropwise to 100 ml of benzene at 60° C. gently at such a rate that nitrogen was continuously generated. After reaction at this temperature for 3 hours, the solution was cooled to room temperature, and benzene was then distilled off under reduced pressure. The obtained light yellow oily product was distilled under reduced pressure (145° C./1 mmHg) to obtain 8.6 g of colorless oily 1,2-bis (isocyanatoethylthio)ethane.

$^1$H-NMR (CDCl$_3$) δ: 3.02 (bs, 4H), 3.44 (m, 4H), 4.18 (m, 4H) IR: 2270 cm$^{-1}$

EXAMPLE 2

Preparation of bis(isocyanatomethylthio)phenylmethane

With 13.5 ml of benzaldehyde was mixed with 60 g of ethyl thioglycolate, and 13.5 ml of concentrated hydrochloric acid was added thereto, followed by reaction at room temperature for 2 days. Next, the reaction product was poured into 400 g of ice water, extracted with 100 ml of ethyl acetate, washed with water, and then dried over anhydrous sodium sulfate. Afterward, the solvent was distilled off under reduced pressure to obtain light yellow oily crude lower alkyl (benzylidenedithio)diacetate derivative. Next, this derivative was dissolved in 50 ml of n-propanol without isolating and purifying it, and 14 g of hydrazine monohydrate was added dropwise thereto, while a solution temperature of 5° C. was maintained. After 2 hours, the produced white crystalline (benzylidenedithio)bis (hydrazinocarbonylmethane) was collected by filtration. Next, the collected crystals were washed with 10 ml of cold ethanol twice. After drying, the dried material was dissolved in 40 ml of water, and then cooled to 5° C. Afterward, 13 g of concentrated hydrochloric acid was added dropwise thereto. Furthermore, a solution obtained by dissolving 8 g of sodium nitrite in 20 ml of water was added dropwise thereto.

After 30 minutes, 90 ml of benzene was added thereto, and the solution was then heated up to room temperature, while vigorously stirred. Next, the resulting organic layer was separated, dried over anhydrous magnesium sulfate, and then added dropwise to 200 ml of benzene at 65° C. gently at such a rate that nitrogen was continuously generated. After reaction at this temperature for 3 hours, the solution was cooled to room temperature and the resulting white precipitate was removed by filtration, and benzene was then distilled off under reduced pressure. The obtained colorless oily product was distilled at 80° C. under a reduced pressure of 0.3 mmHg for 2 hours to remove impurities, thereby obtaining the desired bis(isocyanatomethylthio) phenylmethane.

$^1$H-NMR (CDCl$_3$) δ: 4.42 (m, 4H), 5.04 (s, 1H), 7.28 (m, 5H) IR: 2270 cm$^{-1}$

EXAMPLE 3

Preparation of bis[2-(isocyanatomethylthio)ethyl]sulfide

In 360 ml of methyl ethyl ketone was dissolved 27.8 g of bis(2-mercaptoethyl)sulfide, and the solution was then cooled to 5° C. Next, 32 g of a 45% aqueous sodium hydroxide solution was added dropwise thereto, followed by vigorous stirring. To this solution, 60 g of ethyl bromoacetate was added dropwise, and reaction was then carried out at room temperature for 1 hour. Afterward, 200 ml of ethyl acetate was added thereto, and the solution was washed with 50 ml of an aqueous saturated ammonium chloride solution twice, and then dried over anhydrous sodium sulfate. Afterward, the solvent was distilled off under reduced pressure to obtain 44 g of light yellow oily bis(2-ethyloxycarbonylmethylthioethyl) sulfide. This sulfide was dissolved in 70 ml of isopropanol, and 18 g of hydrazine monohydrate was added dropwise thereto, while a solution temperature of 5° C. was maintained. After 2 hours, the produced white crystalline bis(2-hydrazinocarbonylmethylthioethyl) sulfide was collected by filtration. Next, the collected crystals were washed with 20 ml of cold isopropanol twice and further washed with 10 ml of hexane. After drying, the dried material was dissolved in 150 ml of water and then cooled to 5° C., and 25 g of concentrated hydrochloric acid was then added dropwise thereto. Furthermore, a solution obtained by dissolving 16 g of sodium nitrite in 50 ml of water was added dropwise thereto. After 30 minutes, 150 ml of benzene was added thereto, and the solution was then heated up to room temperature, while vigorously stirred. Next, the resulting organic layer was separated, and then dried over anhydrous magnesium sulfate. Afterward, toluene was added thereto for dilution so as to bring the total volume to 500 ml, and the solution was then slowly heated up to 55° C. to gently carry out reaction so that nitrogen might be continuously generated. After the reaction at 70° C. for 3 hours, the solution was cooled to room temperature and then allowed to stand overnight, and the resulting white precipitate was removed by filtration. Afterward, the solvent was distilled off under reduced pressure. The obtained colorless oily product was distilled at 80° C. under a reduced pressure of 0.3 mmHg for 2 hours to remove impurities, thereby obtaining the desired bis[2-(isocyanatomethylthio)ethyl]sulfide.

$^1$H-NMR (CDCl$_3$) δ: 2.9–3.3 (m, 8H), 4.23 (m, 4H) IR: 2270 cm$^{-1}$

EXAMPLE 4

Preparation of 1,1,2,2-tetrakis(isocyanatomethylthio)ethane

In a mixture of 300 ml of ethanol and 150 ml of toluene was dissolved 25 g of ethanediiridenetetrakisthioacetic acid, and one drop of concentrated sulfuric acid was then added thereto. Next, reaction was carried out for 6 hours under heating reflux, while dehydration was done by molecular sieves. After the completion of the reaction, the solution was cooled to room temperature, washed with 50 ml of an aqueous saturated sodium hydrogencarbonate solution twice, and then dried over anhydrous sodium sulfate. Afterward, the solution was concentrated under reduced pressure to obtain light yellow oily crude tetraethyl ethanediiridenetetrakisthioacetate.

Next, this tetrakis ester derivative was dissolved in 65 ml of isopropanol, and then cooled to 5° C., and 11.5 g of hydrazine monohydrate was added dropwise thereto over 2 hours. The resulting white crystalline 1,1,2,2-tetrakis (hydrazinocarbonylmethylthio)ethane was collected by filtration, and then air-dried.

This 1,1,2,2-tetrakis(hydrazinocarbonylmethylthio) ethane was dissolved in 120 ml of water and then cooled to 5° C., and 25 g of concentrated hydrochloric acid was then added dropwise thereto. Furthermore, a solution obtained by dissolving 16 g of sodium nitrite in 25 ml of water was added dropwise thereto. After 2 hours, 120 ml of benzene was added thereto, and the solution was then heated up to room temperature, while vigorously stirred. Next, the resulting organic layer was separated, and then dried over anhydrous magnesium sulfate. Afterward, this benzene solution was then heated up to 55° C. so slowly that a nitrogen gas was gently generated. After being heated under reflux for 2 hours, the solution was allowed to stand overnight at room temperature. The resulting white precipitate was removed by filtration, and the filtrate was concentrated under reduced pressure. The obtained colorless transparent oily product was distilled at 80° C. under 0.3 mmHg to remove low-boiling impurities, thereby obtaining 9.2 g of colorless transparent oily 1,1,2,2-tetrakis(isocyanatomethylthio) ethane.

$^1$H-NMR (CDCl$_3$) δ: 3.11 (bs, 2H), 4.29 (m, 8H) IR: 2270 cm$^{-1}$

EXAMPLE 5

Preparation of 2,2,5,5-tetrakis(isocyanatomethylthio)-1,4-dithiane

In accordance with a process described in Ann. Chem. 595, p. 101 (1955), 80 g of thioglycolic acid was dissolved in 100 ml of concentrated hydrochloric acid, and a hydrogen chloride gas was then introduced thereinto at 5° C. for 2 hours to saturate the solution therewith. Next, the solution was directly heated up to room temperature and then allowed to stand for 7 days. The resulting white precipitate was collected by filtration, washed with cold water, and then air-dried. Afterward, this material was suspended in 300 ml of ethanol, and an ethyl ether solution of diazomethane was then added dropwise thereto until reaction had been completed, while the solution was vigorously stirred and observation was made by TLC (thin-layer chromatography). Excessive diazomethane was treated with a trace amount of acetic acid, and the reaction solution was then concentrated under reduced pressure to obtain light yellow oily 2,2,5,5-tetrakis(carboxymethylthio)-1,4-dithiane.

Next, this tetrakis ester derivative was dissolved in 120 ml of isopropanol, and 13.2 g of hydrazine monohydrate was added dropwise thereto at 5° C. At this temperature, reaction was carried out for 4 hours, and the resulting white crystalline 2,2,5,5-tetrakis(hydrazinocarbonylmethylthio)-1,4-dithiane was collected by filtration, washed with 30 ml of cold ethanol, and then air-dried. Furthermore, this 2,2,5,5-tetrakis(hydrazinocarbonylmethylthio)-1,4-dithiane was dissolved in 125 ml of water, and 28 g of concentrated hydrochloric acid was then added dropwise thereto, while the solution was cooled on an ice bath. After 30 minutes, a solution obtained by dissolving 17.7 g of sodium nitrite in 55 ml of water was added dropwise thereto. After reaction was carried out at this temperature for 4 hours, 150 ml of benzene was added, followed by vigorous stirring to separate the resulting benzene solution. Next, this benzene solution was dried over anhydrous magnesium sulfate, and then heated up to 55° C. so slowly that a nitrogen gas was gently generated. After being heated under reflux for 2 hours, the solution was allowed to stand overnight at room temperature. The resulting white precipitate was removed by filtration, and the filtrate was then concentrated under reduced pressure. The obtained colorless transparent oily product was treated at 80° C. under 0.3 mmHg to remove low-boiling impurities, thereby obtaining 10.5 g of colorless transparent oily 2,2,5,5-tetrakis(isocyanatomethylthio)-1,4-dithiane.

$^1$H-NMR (CDCl$_3$) δ: 3.22 (m, 4H), 4.30 (m, 8H) IR: 2270 cm$^{-1}$

EXAMPLE 6

Mixed were 35.3 parts (0.186 mol) of bis (isocyanatomethylthio)methane, 26.8 parts (0.124 mol) of 1,2,4-tris(mercaptomethyl)benzene and 0.01% by weight (based on the total amount of the mixture) of dibutyltin dilaurate to obtain a uniform solution, and this solution was then sufficiently defoamed. Afterward, the solution was injected into a lens mold comprising a glass mold and a gasket. In succession, the solution was slowly heated from 40° C. to 120° C. over 20 hours to achieve curing. After the completion of the polymerization, the molded lens was slowly cooled, and then taken out from the mold.

The thus obtained lens was colorless and transparent and had a refractive index $n_d$ of 1.69, an Abbe's number $v_d$ of 31 and a heat deformation start temperature of 112° C. Even when dyed in a dye bath at 95° C., the lens was not deformed.

After dyeing, transmittances of the lens were 30% in the case of ML-Yellow, 38% in the case of ML-Red and 48% in the case of ML-Blue, and the total evaluation of its dyeability was "o" After 48 hours, water absorption was 0.02%, and surface hardness was H.

EXAMPLE 7

Mixed were 30 parts (0.158 mol) of bis (isocyanatomethylthio)methane and 28.9 parts (0.078 mol)

of 4,8-bis(mercaptomethyl)-3,6,9-trithia-1,11-undecanedithiol to obtain a uniform solution, and this solution was then sufficiently defoamed. Afterward, the solution was injected into a lens mold comprising a glass mold and a gasket. In succession, the solution was slowly heated from 30° C. to 120° C. over 23 hours to achieve curing. After the completion of the polymerization, the molded lens was slowly cooled, and then taken out from the mold.

The thus obtained lens was colorless and transparent and had a refractive index $n_d$ of 1.69, an Abbe's number $v_d$ of 32 and a heat deformation start temperature of 107° C. Even when dyed in a dye bath at 95° C., the lens was not deformed.

After dyeing, transmittances of the lens were 28% in the case of ML-Yellow, 32% in the case of ML-Red and 45% in the case of ML-Blue, and the total evaluation of its dyeability was "o". After 48 hours, water absorption was 0.01%, and surface hardness was 2H.

EXAMPLE 8

Mixed were 30 parts (0.158 mol) of bis(isocyanatomethylthio)methane, 27.4 parts (0.105 mol) of 1,2-bis(2-mercaptoethylthio)-3-mercaptopropane and 0.01% by weight (based on the total amount of the mixture) of dibutyltin dilaurate to obtain a uniform solution, and this solution was then sufficiently defoamed. Afterward, the solution was injected into a lens mold comprising a glass mold and a gasket. In succession, the solution was slowly heated from 30° C. to 120° C. over 23 hours to achieve curing. After the completion of the polymerization, the molded lens was slowly cooled, and then taken out from the mold.

The thus obtained lens was colorless and transparent and had a refractive index $n_d$ of 1.68, an Abbe's number $v_d$ of 32 and a heat deformation start temperature of 100° C. Even when dyed in a dye bath at 95° C., the lens was not deformed.

After dyeing, transmittances of the lens were 33% in the case of ML-Yellow, 33% in the case of ML-Red and 41% in the case of ML-Blue, and the total evaluation of its dyeability was "o". After 48 hours, water absorption was 0.02%, and surface hardness was H.

EXAMPLE 9

Mixed were 30 parts (0.158 mol) of bis(isocyanatomethylthio)methane and 15.8 parts (0.079 mol) of 2,2-bis(mercaptomethyl)-1,3-propanedithiol to obtain a uniform solution, and this solution was then sufficiently defoamed. Afterward, the solution was injected into a lens mold comprising a glass mold and a gasket. In succession, the solution was slowly heated from 30° C. to 120° C. over 23 hours to achieve curing. After the completion of the polymerization, the molded lens was slowly cooled, and then taken out from the mold.

The thus obtained lens was colorless and transparent and had a refractive index $n_d$ of 1.69, an Abbe's number $v_d$ of 32 and a heat deformation start temperature of 154° C. Even when dyed in a dye bath at 95° C., the lens was not deformed.

After dyeing, transmittances of the lens were 35% in the case of ML-Yellow, 38% in the case of ML-Red and 46% in the case of ML-Blue, and the total evaluation of its dyeability was "o". After 48 hours, water absorption was 0.01%, and surface hardness was 2H.

EXAMPLE 10

Mixed were 21 parts (0.11 mol) of bis(isocyanatomethylthio)methane, 25 parts (0.068 mol) of 4,8-bis(mercaptomethyl)-3,6,9-trithia-1,11-undecanedithiol and 6.1 parts (0.027 mol) of isophorone diisocyanate to obtain a uniform solution, and this solution was then sufficiently defoamed. Afterward, the solution was injected into a lens mold comprising a glass mold and a gasket. In succession, the solution was slowly heated from 30° C. to 120° C. over 23 hours to achieve curing. After the completion of the polymerization, the molded lens was slowly cooled, and then taken out from the mold.

The thus obtained lens was colorless and transparent and had a refractive index $n_d$ of 1.68, an Abbe's number $v_d$ of 32 and a heat deformation start temperature of 111° C. Even when dyed in a dye bath at 95° C., the lens was not deformed.

After dyeing, transmittances of the lens were 30% in the case of ML-Yellow, 35% in the case of ML-Red and 46% in the case of ML-Blue, and the total evaluation of its dyeability was "o" After 48 hours, water absorption was 0.01%, and surface hardness was H.

EXAMPLE 11

Mixed were 26.0 parts (0.11 mol) of 1,2-bis(isocyanatomethylthio)ethane, 19.5 parts (0.075 mol) of 1,2-bis[(2-mercaptoethyl)thio]-3-mercaptopropane and 0.01% by weight (based on the total amount of the mixture) of dibutyltin dilaurate to obtain a uniform solution, and this solution was then sufficiently defoamed. Afterward, the solution was injected into a lens mold comprising a glass mold and a gasket which had been subjected to a release treatment. In succession, the solution was slowly heated from 40° C. to 120° C. over 20 hours to achieve curing. After the completion of the polymerization, the molded lens was slowly cooled, and then taken out from the mold.

The thus obtained lens was colorless and transparent and had a refractive index $n_d$ of 1.66, an Abbe's number $v_d$ of 33 and a heat deformation start temperature of 100° C.

After dyeing, transmittances of the lens were 30% in the case of ML-Yellow, 34% in the case of ML-Red and 43% in the case of ML-Blue, and the total evaluation of its dyeability was "o". After 48 hours, water absorption was 0.04%, and surface hardness was H.

EXAMPLE 12

Mixed were 22.0 parts (0.095 mol) of 1,2-bis(isocyanatomethylthio)ethane, 14.0 parts (0.062 mol) of 1,2,4-tris(mercaptomethyl)benzene and 0.01% by weight (based on the total amount of the mixture) of dibutyltin dilaurate to obtain a uniform solution, and this solution was then sufficiently defoamed. Afterward, the solution was injected into a lens mold comprising a glass mold and a gasket which had been subjected to a release treatment. In succession, the solution was slowly heated from 40° C. to 120° C. over 20 hours to achieve curing. After the completion of the polymerization, the molded lens was slowly cooled, and then taken out from the mold.

The thus obtained lens was colorless and transparent and had a refractive index $n_d$ of 1.68, an Abbe's number $v_d$ of 31 and a heat deformation start temperature of 122° C.

After dyeing, transmittances of the lens were 34% in the case of ML-Yellow, 39% in the case of ML-Red and 50% in the case of ML-Blue, and the total evaluation of its dyeability was "o" After 48 hours, water absorption was 0.02%, and surface hardness was H.

EXAMPLE 13

Mixed were 30.0 parts (0.12 mol) of 1,2-bis(isocyanatoethylthio)ethane, 16.7 parts (0.077 mol) of 1,2, 4-tris(mercaptomethyl)benzene and 0.01% by weight (based on the total amount of the mixture) of dibutyltin dilaurate to obtain a uniform solution, and this solution was then sufficiently defoamed. Afterward, the solution was injected into a lens mold comprising a glass mold and a gasket which had been subjected to a release treatment. In succession, the solution was slowly heated from 40° C. to 120° C. over 20 hours to achieve curing. After the completion of the polymerization, the molded lens was slowly cooled, and then taken out from the mold.

The thus obtained lens was colorless and transparent and had a refractive index $n_d$ of 1.67, an Abbe's number $v_d$ of 31 and a heat deformation start temperature of 115° C.

After dyeing, transmittances of the lens were 32% in the case of ML-Yellow, 36% in the case of ML-Red and 45% in the case of ML-Blue, and the total evaluation of its dyeability was "o". After 48 hours, water absorption was 0.03%, and surface hardness was H.

EXAMPLE 14

Mixed were 40.0 parts (0.136 mol) of bis[2-(isocyanatomethylthio)ethyl] sulfide, 20.0 parts (0.057 mol) of 1,2,4-tris(mercaptomethyl)benzene and 0.01% by weight (based on the total amount of the mixture) of dibutyltin dilaurate to obtain a uniform solution, and this solution was then sufficiently defoamed. Afterward, the solution was injected into a lens mold comprising a glass mold and a gasket which had been subjected to a release treatment. In succession, the solution was slowly heated from 40° C. to 120° C. over 20 hours to achieve curing. After the completion of the polymerization, the molded lens was slowly cooled, and then taken out from the mold.

The thus obtained lens was colorless and transparent and had a refractive index $n_d$ of 1.67, an Abbe's number $v_d$ of 32 and a heat deformation start temperature of 111° C.

After dyeing, transmittances of the lens were 33% in the case of ML-Yellow, 35% in the case of ML-Red and 43% in the case of ML-Blue, and the total evaluation of its dyeability was "o" After 48 hours, water absorption was 0.04%, and surface hardness was H.

EXAMPLE 15

Mixed were 39.2 parts (0.147 mol) of bis(isocyanatomethylthio)phenylmethane, 25.5 parts (0.098 mol) of 1,2-bis[(2-mercaptoethyl)thio]-3-mercaptopropane and 0.01% by weight (based on the total amount of the mixture) of dibutyltin dilaurate to obtain a uniform solution, and this solution was then sufficiently defoamed. Afterward, the solution was injected into a lens mold comprising a glass mold and a gasket which had been subjected to a release treatment. In succession, the solution was slowly heated from 40° C. to 120° C. over 20 hours to achieve curing. After the completion of the polymerization, the molded lens was slowly cooled, and then taken out from the mold.

The thus obtained lens was colorless and transparent and had a refractive index $n_d$ of 1.68, an Abbe's number $v_d$ of 31 and a heat deformation start temperature of 114° C.

After dyeing, transmittances of the lens were 35% in the case of ML-Yellow, 38% in the case of ML-Red and 49% in the case of ML-Blue, and the total evaluation of its dyeability was "o". After 48 hours, water absorption was 0.04%, and surface hardness was H.

EXAMPLE 16

Mixed were 22 parts (0.052 mol) of 1,1,2,2-tetrakis (isocyanatomethylthio)ethane, 15.1 parts (0.07 mol) of 1,2, 4-tris(mercaptomethyl)benzene and 0.01% by weight (based on the total amount of the mixture) of dibutyltin dilaurate to obtain a uniform solution, and this solution was then sufficiently defoamed. Afterward, the solution was injected into a lens mold comprising a glass mold and a gasket which had been subjected to a release treatment. In succession, the solution was slowly heated from 40° C. to 120° C. over 20 hours to achieve curing. After the completion of the polymerization, the molded lens was slowly cooled, and then taken out from the mold.

The thus obtained lens was colorless and transparent and had a refractive index $n_d$ of 1.70 and an Abbe's number $v_d$ of 30. A heat deformation start temperature was not definitely confirmed until 200° C. After dyeing by the use of 2% benzyl alcohol as a carrier, transmittances of the dyed lens were 34% in the case of ML-Yellow, 42% in the case of ML-Red and 48% in the case of ML-Blue, and the total evaluation of its dyeability was "o" After 48 hours, water absorption was 0.01%, and surface hardness was 2H.

EXAMPLE 17

Mixed were 22 parts (0.052 mol) of 1,1,2,2-tetrakis (isocyanatomethylthio)ethane and 19.3 parts (0.052 mol) of 4,8-bis(mercaptomethyl)-3,6,9-trithia-1,11-undecanedithiol to obtain a uniform solution, and this solution was then sufficiently defoamed. Afterward, the solution was injected into a mold comprising a glass mold and a gasket which had been subjected to a release treatment. In succession, the solution was slowly heated from 30° C. to 120° C. over 23 hours to achieve curing. After the completion of the polymerization, the molded lens was slowly cooled, and then taken out from the mold.

The thus obtained lens was colorless and transparent and had a refractive index $n_d$ of 1.71 and an Abbe's number $v_d$ of 30. A heat deformation start temperature was not definitely confirmed until 200° C. After dyeing by the use of 2% benzyl alcohol as a carrier, transmittances of the dyed lens were 29% in the case of ML-Yellow, 36% in the case of ML-Red and 45% in the case of ML-Blue, and the total evaluation of its dyeability was "o". After 48 hours, water absorption was 0.01%, and surface hardness was 2H.

EXAMPLE 18

Mixed were 21 parts (0.05 mol) of 1,1,2,2-tetrakis (isocyanatomethylthio)ethane, 17.3 parts (0.067 mol) of 1,2-bis[(2-mercaptoethyl)thio]-3-mercaptopropane and 0.01% by weight (based on the total amount of the mixture) of dibutyltin dilaurate to obtain a uniform solution, and this solution was then sufficiently defoamed. Afterward, the solution was injected into a lens mold comprising a glass mold and a gasket which had been subjected to a release treatment. In succession, the solution was slowly heated from 40° C. to 120° C. over 20 hours to achieve curing. After the completion of the polymerization, the molded lens was slowly cooled, and then taken out from the mold.

The thus obtained lens was colorless and transparent and was excellent in impact resistance, and it had a refractive index $n_d$ of 1.69, an Abbe's number $v_d$ of 31 and a heat deformation start temperature of 179° C. After dyeing by the use of 2% benzyl alcohol as a carrier, transmittances of the dyed lens were 30% in the case of ML-Yellow, 37% in the case of ML-Red and 45% in the case of ML-Blue, and the total evaluation of its dyeability was "o". After 48 hours, water absorption was 0.01%, and surface hardness was 2H.

EXAMPLE 19

Mixed were 48.1 parts (0.092 mol) of 2,2,5,5-tetrakis (isocyanatomethylthio)-1,4-dithiane, 26.7 parts (0.123 mol)

of 1,2,4-tris(mercaptomethyl)benzene and 0.01% by weight (based on the total amount of the mixture) of dibutyltin dilaurate to obtain a uniform solution, and this solution was then sufficiently defoamed. Afterward, the solution was injected into a lens mold comprising a glass mold and a gasket which had been subjected to a release treatment. In succession, the solution was slowly heated from 40° C. to 120° C. over 20 hours to achieve curing. After the completion of the polymerization, the molded lens was slowly cooled, and then taken out from the mold.

The thus obtained lens was colorless and transparent and had a refractive index $n_d$ of 1.69, an Abbe's number $v_d$ of 31. A heat deformation start temperature was not definitely confirmed until 200° C. After dyeing by the use of 2% benzyl alcohol as a carrier, transmittances of the dyed lens were 36% in the case of ML-Yellow, 41% in the case of ML-Red and 49% in the case of ML-Blue, and the total evaluation of its dyeability was "o" After 48 hours, water absorption was 0.01%, and surface hardness was 2H.

EXAMPLE 20

Mixed were 66.8 parts (0.128 mol) of 2,2,5,5-tetrakis (isocyanatomethylthio)-1,4-dithiane, 44.5 parts (0.17 mol) of 1,2-bis[(2-mercaptoethyl)thio]-3-mercaptopropane and 0.01% by weight (based on the total amount of the mixture) of dibutyltin dilaurate to obtain a uniform solution, and this solution was then sufficiently defoamed. Afterward, the solution was injected into a lens mold comprising a glass mold and a gasket which had been subjected to a release treatment. In succession, the solution was slowly heated from 40° C. to 120° C. over 20 hours to achieve curing. After the completion of the polymerization, the molded lens was slowly cooled, and then taken out from the mold.

The thus obtained lens was colorless and transparent and had a refractive index $n_d$ of 1.68, an Abbe's number $v_d$ of 31 and a heat deformation start temperature of 170° C. After dyeing by the use of 2% benzyl alcohol as a carrier, transmittances of the dyed lens were 32% in the case of ML-Yellow, 33% in the case of ML-Red and 44% in the case of ML-Blue, and the total evaluation of its dyeability was "o" After 48 hours, water absorption was 0.01%, and surface hardness was 2H.

COMPARATIVE EXAMPLE 1

Mixed were 25.3 parts (0.147 mol) of bis(2-isocyanatoethyl) sulfide and 25.5 parts (0.098 mol) of 1,2-bis[(2-mercaptoethyl)thio]-3-mercaptopropane to obtain a uniform solution, and this solution was then sufficiently defoamed. Afterward, the solution was injected into a lens mold comprising a glass mold and a gasket which had been subjected to a release treatment. In succession, the solution was slowly heated from 40° C. to 120° C. over 20 hours to achieve curing. After the completion of the polymerization, the molded lens was slowly cooled, and then taken out from the mold.

The thus obtained lens was colorless and transparent and had a refractive index $n_d$ of 1.63, an Abbe's number $v_d$ of 36 and a heat deformation start temperature of 106° C.

After dyeing, transmittances of the lens were 31%, in the case of ML-Yellow, 33% in the case of ML-Red and 46% in the case of ML-Blue, and the total evaluation of its dyeability was "o". After 48 hours, water absorption was 0.04%, and surface hardness was H.

In Comparative Example 1, the combination of the isocyanate having two NCO groups and 1,2-bis[(2-mercaptoethyl)thio]-3-mercaptopropane was employed, and when Comparative Example 1 is compared with Examples 8, 11 and 15, it is apparent that refractive indexes of these examples are as high as 1.68, 1.66 and 1.68, respectively, but that of Comparative Example 1 was low, 1.63.

COMPARATIVE EXAMPLE 2

Mixed were 44 parts (0.16 mol) of bis (isocyanatomethylthio)-(3-isocyanatopropyl)methane and 28 parts (0.107 mol) of 1,2-bis[(2-mercaptoethyl)thio]-3-mercaptopropane to obtain a uniform solution, and this solution was then sufficiently defoamed. Afterward, the solution was injected into a lens mold comprising a glass mold and a gasket which had been subjected to a release treatment. In succession, the solution was slowly heated from 40° C. to 120° C. over 20 hours to achieve curing. After the completion of the polymerization, the molded lens was slowly cooled, and then taken out from the mold.

The thus obtained lens was colorless and transparent and had a refractive index $n_d$ of 1.65, an Abbe's number $v_d$ of 34 and a heat deformation start temperature of 130° C.

After dyeing, transmittances of the lens were 45% in the case of ML-Yellow, 58% in the case of ML-Red and 58% in the case of ML-Blue, and the dyeing was not accomplished and so the total evaluation of its dyeability was "x" After the dyeing by the use of 2% benzyl alcohol as a carrier, the transmittances of the lens were 28% in the case of ML-Yellow, 31% in the case of ML-Red and 35% in the case of ML-Blue, and the total evaluation of its dyeability was "o". After 48 hours, water absorption was 0.04%, and surface hardness was H.

In this Comparative Example 2, the combination of the isocyanate having three NCO groups and 1,2-bis[(2-mercaptoethyl)thio]-3-mercaptopropane is employed, but in the present invention, it is not required to use the isocyanate having three NCO groups. When the lens obtained in Comparative Example 2 is compared with the lenses obtained in Examples 8, 11 and 15 in which the combination of the isocyanate having two NCO groups and 1,2-bis[(2-mercaptoethyl)thio]-3-mercaptopropane is employed, it is apparent that the lens of Comparative Example 2 is more excellent in heat resistance but the lenses of the examples are more excellent in the refractive index and the dyeability.

Furthermore, the lens of Comparative Example 2 is poor in both of the refractive index and the heat resistance, as compared with those of the example of the isocyanate having four NCO groups (Example 18).

COMPARATIVE EXAMPLE 3

Mixed were 33.9 parts (0.147 mol) of 2,5-bis (isocyanatomethyl)-1,4-dithiane and 25.5 parts (0.098 mol) of 1,2-bis[(2-mercaptoethyl)thio]-3-mercaptopropane to obtain a uniform solution, and this solution was then sufficiently defoamed. Afterward, the solution was injected into a lens mold comprising a glass mold and a gasket which had been subjected to a release treatment. In succession, the solution was slowly heated from 40° C. to 120° C. over 20 hours to achieve curing. After the completion of the polymerization, the molded lens was slowly cooled, and then taken out from the mold.

The thus obtained lens was colorless and transparent and had a refractive index $n_d$ of 1.67, an Abbe's number $v_d$ of 33 and a heat deformation start temperature of 126° C.

After dyeing, transmittances of the lens were 35% in the case of ML-Yellow, 35% in the case of ML-Red and 46% in the case of ML-Blue, and the total evaluation of its dyeability was "o" After 48 hours, water absorption was 0.04%, and surface hardness was H.

In this Comparative Example 3, the combination of 1,2-bis[(2-mercaptoethyl)thio]-3-mercaptopropane and the isocyanate having a 1,4-dithiane ring and two NCO groups is employed, but since this isocyanate has the dithiane ring, a refractive index and heat resistance equal to those of the present invention can be imparted to the lens, though the compound has two NCO groups. However, as compared with Example 20 in which the isocyanate having the same dithiane ring is used, the lens of Comparative Example 3 is noticeably poor.

As described above, according to the present invention, a specific polyisocyanate is used, whereby optical materials such as plastic lenses having a very high refractive index and heat resistance can be provided.

What is claimed is:

1. A composition for optical materials which comprises the following two components (a) and (b):

(a) a component containing at least one of polyisocyanates represented by the following formula (1):

  (1)

wherein A is an alkanediyl group or an alkanetetrayl group which may contain a sulfur atom, or a dithianetetrayl group, and the alkanediyl group or the alkanetetrayl group may be substituted by a phenyl group; B is a methylene chain represented by $-(CH_2)_m-$ (m is an integer of 1 to 4) which may contain a sulfur atom, and Bs may be the same or different; and n is an integer of 2 or 4, and (b) a component containing at least one of polythiols having two or more mercapto groups.

2. The composition for optical materials according to claim 1 wherein the polyisocyanate is a polyisocyanate represented by the following formula (2):

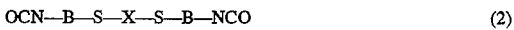  (2)

wherein X is a lower alkanediyl group having 1 to 4 carbon atoms which may contain a sulfur atom, and this alkanediyl group may be substituted by a phenyl group; and B is a methylene chain represented by $-(CH_2)_m-$ (m is an integer of 1 to 4) which may contain a sulfur atom, and Bs may be the same or different.

3. The composition for optical materials according to claim 1 wherein the polyisocyanate is a polyisocyanate represented by the following formula (3):

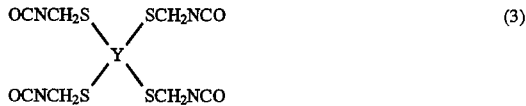  (3)

wherein Y is a lower alkanetetrayl group or a dithianetetrayl group which may contain a sulfur atom.

4. A plastic lens having a high refractive index obtained by polymerizing the composition for the optical materials described in claim 1.

5. A plastic lens having a high refractive index obtained by polymerizing the composition for the optical materials described in claim 2.

6. A plastic lens having a high refractive index obtained by polymerizing the composition for the optical materials described in claim 3.

* * * * *